(12) United States Patent
Brown et al.

(10) Patent No.: US 8,354,565 B1
(45) Date of Patent: Jan. 15, 2013

(54) RAPID GAS HYDRATE FORMATION PROCESS

(75) Inventors: Thomas D. Brown, Finleyville, PA (US); Charles E. Taylor, Pittsburgh, PA (US); Alfred J. Unione, Pittsburgh, PA (US)

(73) Assignee: U.S. Department of Energy, Washington, DC (US)

( * ) Notice: Subject to any disclaimer, the term of this patent is extended or adjusted under 35 U.S.C. 154(b) by 192 days.

(21) Appl. No.: 12/814,660

(22) Filed: Jun. 14, 2010

(51) Int. Cl.
*C07C 7/20* (2006.01)
*C07C 9/00* (2006.01)

(52) U.S. Cl. .......................................................... 585/15
(58) Field of Classification Search ............... 585/15
See application file for complete search history.

(56) References Cited

U.S. PATENT DOCUMENTS

| | | | |
|---|---|---|---|
| 5,536,893 A | 7/1996 | Gudmundsson | |
| 6,028,234 A * | 2/2000 | Heinemann et al. | 585/15 |
| 6,111,155 A * | 8/2000 | Williams et al. | 585/15 |
| 6,180,843 B1 * | 1/2001 | Heinemann et al. | 585/15 |
| 6,653,516 B1 | 11/2003 | Yoshikawa et al. | |
| 7,863,491 B1 * | 1/2011 | Bonso | 585/15 |
| 7,947,857 B2 * | 5/2011 | Nazari et al. | 585/15 |
| 7,964,150 B2 * | 6/2011 | Balczewski | 422/129 |
| 8,043,579 B2 * | 10/2011 | Katoh et al. | 422/232 |
| 8,056,832 B2 * | 11/2011 | Hsieh et al. | 239/311 |
| 8,138,382 B2 * | 3/2012 | Kanda et al. | 585/15 |
| 8,153,075 B2 * | 4/2012 | Nagamori et al. | 422/201 |
| 2011/0064643 A1 * | 3/2011 | Lee et al. | 423/437.1 |
| 2011/0217210 A1 * | 9/2011 | Katoh et al. | 422/162 |
| 2011/0263913 A1 * | 10/2011 | Lee et al. | 585/15 |

OTHER PUBLICATIONS

Matsuda et al, "Hydrate Formation Using Water Spraying onto a Cooled Solid Surface in a Guest Gas," AIChE Journal, vol. 52, No. 8, Aug. 2006.
Kumar et al., "Studies on Pneumatic Atomization," Ind. Eng. Chem. Process Des. Develop., vol. 10(3) (1971).
Sovani et al., "Effervescent atomization," Progress in Energy and Combustion Science 27 (2001).
Brown et al., "Rapid Gas Hydrate Formation Processes: Will They Work?," Energies 3 (2010).

* cited by examiner

*Primary Examiner* — Ellen McAvoy
(74) *Attorney, Agent, or Firm* — James B. Potts; Mark P. Dvorscak; John T. Lucas (57) ABSTRACT

The disclosure provides a method and apparatus for forming gas hydrates from a two-phase mixture of water and a hydrate forming gas. The two-phase mixture is created in a mixing zone which may be wholly included within the body of a spray nozzle. The two-phase mixture is subsequently sprayed into a reaction zone, where the reaction zone is under pressure and temperature conditions suitable for formation of the gas hydrate. The reaction zone pressure is less than the mixing zone pressure so that expansion of the hydrate-forming gas in the mixture provides a degree of cooling by the Joule-Thompson effect and provides more intimate mixing between the water and the hydrate-forming gas. The result of the process is the formation of gas hydrates continuously and with a greatly reduced induction time. An apparatus for conduct of the method is further provided.

18 Claims, 8 Drawing Sheets

RAPID GAS HYDRATE FORMATION PROCESS

STATEMENT OF GOVERNMENTAL SUPPORT

The United States Government has rights in this invention pursuant to the employer-employee relationship of the Government to the inventors as U.S. Department of Energy employees and site-support contractors at the National Energy Technology Laboratory.

TECHNICAL FIELD

The disclosure provides a method and apparatus for forming gas hydrates from a two-phase mixture of water and a hydrate forming gas. The two-phase mixture is created in a mixing zone which may be wholly included within the body of a spray nozzle. The two-phase mixture is subsequently sprayed into a reaction zone under pressure and temperature conditions suitable for formation of the gas hydrate. The reaction zone pressure is less than the mixing zone pressure so that expansion of the hydrate-forming gas in the mixture provides a degree of cooling by the Joule-Thompson effect and provides more intimate mixing between the water and the hydrate-forming gas. The result of the process is the formation of gas hydrates continuously and with a greatly reduced induction time. An apparatus for conduct of the method is further provided.

BACKGROUND OF THE INVENTION

Clathrates are non-stoichiometric crystalline compounds consisting of two molecular species, where one species physically entraps the other within a cage-like structure. The species forming the cage-like structure is commonly referred to as the host, while the caged component is commonly referred to as the guest. When the cage-like structure is made up of water molecules bonded together, the crystalline compounds formed are known as clathrate hydrates or gas hydrates.

In gas hydrates, the host-lattice is created by water molecules connected together through hydrogen bonding. The guest molecule is held in place inside cavities of the hydrogen-bonded water molecules, and the lattice is stabilized by van der Weals forces between host and guest molecules without chemical bonding between the host-lattice and guest molecule. The host-lattice is thermodynamically unstable without the presence of a guest molecule in the cavity, and without the support of the trapped molecules, the lattice structure of gas hydrates will collapse into conventional ice crystal structures or liquid water. Most low molecular weight gases, including $O_2$, $H_2$, $N_2$, $CO_2$, $CH_4$, $H_2S$, Ar, Kr, and Xe as well as some higher hydrocarbons and freons, will form hydrates at suitable temperatures and pressures. The storage capacity for gas in these structures is considerable, and gas hydrates are attractive options for the storing and transportation natural gas and other gases as an alternative to liquefying or compression.

Formation and decomposition of gas hydrates are first order phase transitions rather than chemical reactions, and generally the typical mechanism of hydrate formation in a pure water-gas system proceeds by water molecules first forming clusters by hydrogen bonding in the liquid phase, and then proceeding to cluster and occlude gas until a critical size of the clusters is reached. As is known in the art, hydrate nucleation refers to the process where hydrate nuclei, grow and disperse until they attain the critical size. If the size of the nuclei is less than the critical size, the nuclei are unstable and may continue to grow or break in the aqueous solution. If the growing nuclei reach the critical size they then becomes stable, which leads to the formation of hydrate crystals. This period from when the hydrate nuclei are forming and dissolving to the time when the nuclei reach the critical size is called the induction time. Induction times exceeding 6 hours are not uncommon. Because the water and hydrate forming gas must be maintained at the temperature and pressure condition for hydrate formation during the induction time, this requirement can generate large capital costs and is of paramount importance.

As a result, reducing the induction time and increasing the rate of hydrate production are significant areas of interest in hydrate forming technologies. Generally speaking, efforts concentrate on improvements in the two conditions that need to be satisfied in order to produce a high rate of hydrate formation: (1) a good mixing of the hydrate-forming gas and water, and (2) an effective cooling for removing the heat released by the exothermic hydrate formation. A primary means of optimizing these conditions has been through utilization of mechanisms generally termed water-spraying reactors.

In a water-spraying reactor, liquid water is sprayed in a continuous phase of a hydrate-forming gas or gases. Typically, water is sprayed downward by an atomizer into the hydrate-forming gas, which is confined in a vertically oriented cylindrical cell with its side wall being cooled from the outside. See e.g., U.S. Pat. No. 5,536,893, issued Jun. 16, 1996, issued to Gudmundsson, among others. This methodology has been successful in the production of gas hydrates, however the basic approach has disadvantages in both effective cooling and mixing. The cooling mechanism is mainly based on spray-to-wall heat transfer, and this mechanism may become increasingly ineffective with an increase in the reactor size. Additionally, in a reactor equipped with multiple spray nozzles, many of the water sprays formed may be away from the wall of the reactor, and may be minimally cooled.

Another method of cooling is utilization of impingement heat transfer from sprayed water to the surface of a cooled, highly heat-conductive slab, so that heat released by gas hydrate formation on the slab is directly removed by heat conduction into the slab. See Matsuda et al., "Hydrate Formation Using Water Spraying onto a Cooled Solid Surface in a Guest Gas," *AIChE Journal*, Vol. 52, No. 8 (August 2006). This approach can suffer from formation of a gas hydrate layer on the metal block surface, acting to hindering the heat flow into the block.

An alternative approach involves a water spray, collection of the water accumulated at the bottom of the reactor, and pumping the accumulated water to an external heat exchanger to be cooled and reintroduced to the reactor to be sprayed again. See e.g., U.S. Pat. No. 6,653,516, issued Nov. 25, 2003, issued to Yoshikawa, et al. The cooled circulating water compensates for the heat released by the hydrate formation, and the rate of water circulation is varied in proportion to the capacity of the reactor. However, obstructing the water-circulation loop due to hydrate formation is a significant risk, and the water flow rate through the loop may need to be maintained at an excessively high-level as compared to the rate of water consumption due to the hydrate formation. This increases the pumping power requirement.

The foregoing methods also introduce water and the hydrate-forming gas into the reactor separately, and rely on mixing within the reactor itself in order to generate sufficient contact between the water and gas. Various methods have been utilized to improve the mixing process and thereby increase the rate of hydrate formation, including stirring mechanisms and other similar processes that apply shear forces to gas bubbles in the mixture. These processes act to decrease bubble size and increase the contact between water in the reactor and the hydrate-forming gas, however the means by which the shear force is generated and applied adds additional mechanical and operational complication to the reactor.

Efforts to increase the rate of methane hydrate formation with a spray of water and dissolved methane have also been investigated, in order to obtain memory effects and reduce induction time. See '516 to Yoshikawa, et al; See also Holder et al., "Formation of gas hydrates from single-phase aqueous solutions," *Chemical Engineering Science* 56 (2001); See also Lee et al., "Methane—ethane and methane—propane hydrate formation and decomposition on water droplets," *Chemical Engineering Science, Vol.* 60 (2005). However, many hydrate forming gases such as methane have extremely low solubility in water and the production of a single-phase system consisting of liquid water and a dissolved hydrate-forming gas presents additional difficulties not encountered when hydrate formation can be effectively accomplished using separate phases of liquid water and a gaseous hydrate-former.

It would be advantageous to provide a process whereby the exothermic heat of gas hydrate formation could be more effectively removed without reliance on contact between reactor walls or other heat transfer surfaces, and without reliance on water sub-cooling systems generating significant parasitic loads. Further, it would be advantageous to provide a process whereby water and a gas-forming hydrate could be introduced into a hydrate-forming reactor as a mixture, so that reliance on shear forces or water-gas intermingling for mixing within the reactor itself could be mitigated. Further, it would be advantageous to provide a process compatible with the water-gas mixture entering the reactor in a two-phase state, so that difficulties associated with producing a single-phase system consisting of liquid water with dissolved hydrate could be avoided. Further, it would be advantageous to provide a process whereby some degree of exothermic heat removal could be accommodated by the thermodynamic response of the mixture to the hydrate reactor conditions, and where that response could simultaneously aid in further contact between the water and the hydrate-forming gas of the mixture.

Accordingly, it is an object of this disclosure to provide a method and apparatus for the formation of gas hydrates where the exothermic heat of gas hydrate formation can be more effectively removed without reliance on contact between reactor walls or other heat transfer surfaces.

Further, it is an object of this disclosure to provide a method and apparatus for the formation of gas hydrates where the exothermic heat of gas hydrate formation can be more effectively removed without reliance on circulating water sub-cooling systems generating significant parasitic loads.

Further, it is an object of this disclosure to provide a method and apparatus for the formation of gas hydrates where water and a gas-forming hydrate can be introduced into a hydrate-forming reactor as a mixture, so that reliance on shear forces for mixing within the reactor itself can be mitigated.

Further, it is an object of this disclosure to provide a method and apparatus for the formation of gas hydrates compatible with the water-gas mixture entering the reactor in a two-phase state, so that difficulties associated with producing a single-phase system consisting of liquid water with dissolved hydrate can be avoided.

Further, it is an object of this disclosure to provide a method and apparatus for the formation of gas hydrates where some degree of exothermic heat removal can be accommodated by the thermodynamic response of the mixture to the hydrate reactor conditions, and where that response can simultaneously aid in further contact between the water and the hydrate-forming gas of the mixture.

These and other objects, aspects, and advantages of the present disclosure will become better understood with reference to the accompanying description and claims.

SUMMARY OF INVENTION

The disclosure herein provides a method and apparatus for forming gas hydrates from a two-phase mixture of water and a hydrate forming gas through the introduction of the two-phase mixture into a reaction zone, where the reaction zone is under pressure and temperature conditions suitable for formation of the gas hydrate. The method briefly entails:

(a) injecting water into a mixing zone at a water injection rate;

(b) injecting a gaseous stream comprised of a hydrate-forming gas into the mixing zone at a gas injection rate, and forming a water-gas mixture having a water-gas pressure in the mixing zone; and (c) spraying the water-gas mixture into a reaction zone, where the reaction zone temperature is less than the equilibrium hydrate formation temperature for the reaction zone pressure, and where the reaction zone pressure is reduced below the water-gas mixture pressure, such the hydrate-forming gas expands, and the expansion cools some portion of the water-gas spray droplets to at least the equilibrium hydrate formation temperature, thereby forming the gas hydrate.

The reaction zone pressure is less than the mixing zone pressure so that the expansion of the hydrate-forming gas which occurs in response to the lower reaction zone pressure provides a degree of cooling by the Joule-Thompson effect. Further, the expansion of the hydrate-forming gas serves to expand water-gas bubbles in the droplets, breaking up the bubbles and producing more intimate mixing between the water and the hydrate-forming gas. The result of the process is the formation of gas hydrates continuously and with a greatly reduced induction time.

An apparatus for conduct of the method is further provided. The novel apparatus and principles of operation are further discussed in the following description.

DETAILED DESCRIPTION OF THE PREFERRED EMBODIMENTS

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide a method and apparatus for forming gas hydrates from a two-phase mixture of water and a hydrate forming gas through the introduction of the two-phase mixture into a reaction zone, where the reaction zone is under pressure and temperature conditions suitable for formation of the gas hydrate.

The method briefly entails:

(a) injecting water into a mixing zone at a water injection rate;

(b) injecting a gaseous stream comprised of a hydrate-forming gas into the mixing zone at a gas injection rate, and forming a water-gas mixture having a water-gas pressure in the mixing zone; and (c) spraying the water-gas mixture into a reaction zone, where the reaction zone temperature is less than the equilibrium hydrate formation temperature for the reaction zone pressure, and where the reaction zone pressure is reduced below the water-gas pressure, such that the hydrate-forming gas expands, and the expansion cools and maintains some portion of the water-gas spray droplets to at least the equilibrium hydrate formation temperature, thereby forming the gas hydrate.

The water-gas mixture is sprayed into the reaction zone so that the water-gas mixture enters the reaction zone as a plurality of water-gas droplets. The reaction zone pressure is less than the mixing zone pressure so that a motive force for the spray is present, and also so that the expansion of the hydrate-forming gas which occurs in response to the lower reaction zone pressure provides a degree of cooling by the Joule-Thompson effect, reducing the temperature of the water-gas droplets and serving to remove some degree of exothermic heat generated by gas hydrate formation. Further, the expansion of the hydrate-forming gas serves to expand water-gas bubbles in the droplets, breaking up the bubbles and producing more intimate mixing between the water and the hydrate-forming gas. The result of the process is the formation of gas hydrates continuously and with a greatly reduced induction time.

Any gas hydrate formation which may occur in the mixing zone is greatly mitigated through control of water and gas flow rates. Gas hydrates which may form in the mixing zone are greatly limited in size by brief residence time in the mixing zone, and the gas hydrates are swept out of the mixing zone into the reaction zone by the motive force of the water-gas mixture. The formation of gas hydrate within the mixing zone and any subsequent break-up through a spray-producing nozzle may provide nucleation sites for further gas hydrate formation within the reaction zone.

An apparatus for conduct of the method is further provided. The apparatus is comprised of: an enclosure serving as the mixing zone; a water flow path into the enclosure, a gas flow path into the enclosure; means for controlling the water and gas flow rates, a spray orifice capable expelling a flow from the enclosure as a plurality of fluid droplets; a hydrate vessel serving as the reaction zone; and a refrigeration means in thermal communication with the hydrate vessel for control of hydrate vessel conditions. The enclosure serving as the mixing zone and the spray orifice may be incorporated within the body of a single spray nozzle, greatly reducing any physical footprint required.

These and other aspects and advantages of the apparatus will become better understood with reference to the following description and claims.

Principles of the Method and Apparatus

Figure 1:
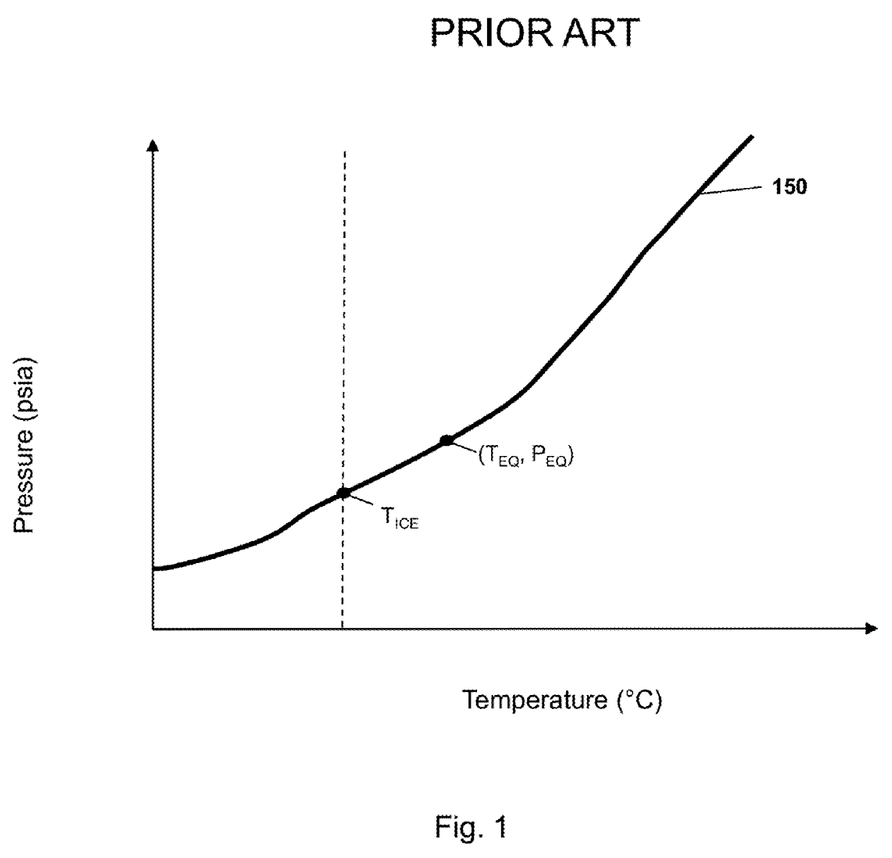
FIG. 1 illustrates a pressure-temperature diagram showing a hydrate stability curve.

FIG. 1 illustrates a general phase diagram for a hydrate-forming gas and water with respect to temperature and pressure as shown. FIG. 1 illustrates hydrate stability curve 150, where hydrate stability curve 150 consists of points defined by hydrate formation temperatures and hydrate formation pressures for the hydrate-forming gas and water system, such as the point ($T_{EQ}$, $P_{EQ}$) as shown. The area above the hydrate stability curve 150 indicates conditions where gas hydrate formation and in some cases, hydrate and water not utilized in hydrate formation is expected, while the area below the hydrate stability curve 150 indicates conditions where gas hydrate formation would not be expected. The area to the left of the vertical passing through $T_{ICE}$ (273K or 0.0° C.) on the hydrate stability curve 150 indicates conditions where hydrate formation plus ice would be expected. Hydrate-stability curve 150 thus marks the limits to gas hydrate formation, as is understood in the art.

As used herein, the "equilibrium hydrate formation temperature" for the gas hydrate refers to the hydrate formation temperature associated with the hydrate formation pressure on hydrate stability curve 150. For example, the temperature $T_{EQ}$ when the hydrate-forming gas and water system at a pressure of $P_{EQ}$, as illustrated at FIG. 1.

As a Gas-Water mixture crosses hydrate stability curve 150 into a region where gas hydrate formation is expected (including at, or to the left or right of $T_{ICE}$), gas hydrate formation occurs within the mixture and exothermic heat from the gas hydrate formation is released. As is known in the art, the continued removal of exothermic heat generated during gas hydrate formation is of paramount importance in any gas hydrate formation method or apparatus. Additionally, the quality of mixing between the gas and the water has a significant impact on the kinetics of gas hydrate formation, and creating a close proximity between the hydrate forming components under the proper pressure and temperature condition is also a primary concern. Generally speaking, the two conditions of (1) a good mixing of the hydrate-guest gas and water and (2) an effective cooling for removing the heat released by the hydrate formation must be satisfied to produce a high rate of hydrate formation. Because growth rates are determined by the rate of supply of the hydrate-forming species as well as the rate of removal of the exothermic heat of formation, the rate of hydrate formation is greatly increased using the method disclosed, which accomplishes both primary ends through gaseous expansion of the hydrate forming gas in a water-gas mixture.

Within the novel method and apparatus disclosed herein, a water-gas mixture comprised of water and a hydrate-forming gas is created in a mixing zone. The water-gas mixture is sprayed from the mixing zone into a lower pressure reaction zone, such that the water-gas mixture is comprised of gas bubbles surrounded by a water film as it enters the reaction zone, The reduced pressure of the reaction zone provides for expansion of the hydrate-forming gas comprising the water-gas mixture. The gaseous expansion provides for cooling of the water-gas mixture through the Joule-Thompson effect, as well as serving to further mix the water-gas mixture as the expansion breaks the water film, so smaller droplets are produced while further increasing the close proximity between the water and the hydrate-forming gas. The novel method thereby accomplishes a good mixing of the hydrate-guest gas and water and an effective cooling for removing the heat released by the hydrate formation through the gaseous expansion, and gas hydrate production is greatly increased. In an embodiment, the method and apparatus forms gas hydrates within the area above hydrate stability curve 150 and to the right of the vertical line passing through $T_{ICE}$, at conditions where gas hydrate formation dominates, but the method and apparatus may be operated within the area above hydrate stability curve 150 and to the left of the vertical line passing through $T_{ICE}$, where both gas hydrate and water ice would form.

Description of the Method

Figure 2:
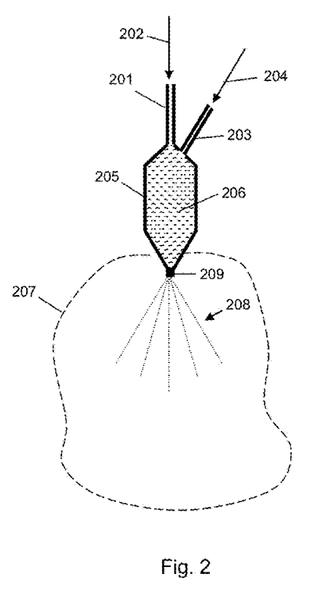
FIG. 2 illustrates the method of forming a gas hydrate.

The method of forming a gas hydrate is illustrated at FIG. 2. FIG. 2 shows water flow path 201 providing a water flow 202. Water flow 202 is provided by water flow path 201 at a water injection rate, and water flow 202 is at a water temperature and a water pressure. FIG. 2 further illustrates gas flow path 203 providing a gaseous stream 204. Gaseous stream 204 is comprised of the hydrate-forming gas, and may be further comprised of additional constituents. Gaseous stream 204 is provided by gas flow path 203 at a gas injection rate, and gaseous stream 204 is at a gas temperature and a gas pressure.

The water temperature, water pressure, and water injection rate, as well as the gas temperature, gas pressure, and gas injection rate, are not limiting within this method, except to the extent that the respective parameters must be sufficient such that the combination of water flow 202 and gaseous stream 204 produces a condition as outlined below.

Water flow 202 and gaseous stream 204 enter mixing zone 205, and form water-gas mixture 206 within mixing zone 205. The injection of water flow 202 and gaseous stream 204 produces a substantially two-phase, heterogeneous liquid-gas mixture. Water-gas mixture 206 may further contain some degree of single phase mixing as a result of incidental gas dissolution within the water.

It is preferable if liquid from water flow 202 and the hydrate-forming gas from gaseous stream 204 form a blend such that the water-gas mixture 206 is comprised of a plurality of bubbles of the hydrate forming gas surrounded by interstitial liquid water. This can be accomplished by consideration of mixing zone 205 characteristics and the water and gas injection rates. The water and gas injection rates into mixing zone 205 can be maintained such that the flow rate of the resulting water-gas mixture through mixing zone 205 limits subsequent separation of the water and the hydrate forming gas through the buoyancy of the hydrate forming gas.

Having formed water-gas mixture 206, water-gas mixture 206 exits mixing zone 205 and enters reaction zone 207 as spray 208, such that the water-gas mixture enters reaction zone 207 as a plurality of water-gas droplets. This may be accomplished through means such as spray orifice 209. Reaction zone 207 has a reaction zone temperature and a reaction zone pressure, where the reaction zone temperature is less than the equilibrium hydrate formation temperature for the gas hydrate at the reaction zone pressure. Further, the reaction zone pressure is less than the water-gas pressure of water-gas mixture 206 entering reaction zone 207 such that the hydrate-forming gas comprising the plurality of water-gas droplets expands, and the expansion of the hydrate-forming gas cools at least some portion of the plurality of water-gas droplets to a temperature less than the equilibrium hydrate formation temperature. Additionally, from the mixing action within mixing zone 205, the plurality of droplets are expected to enter reaction zone 207 as bubbles of the hydrate forming gas surrounded by a film of liquid water, so that as the expansion of the hydrate-forming gas in reaction zone 207 continues, the hydrate forming gas disrupts the film of liquid water, producing droplets reduced in size while increasing the proximity of the hydrate-forming gas and the water within reaction zone 207. As a result of the increased proximity and cooling through gaseous expansion, gas hydrate growth and formation occurs. The exothermic heat released from the formation of the gas hydrates is additionally absorbed by the expansion of the hydrate-forming gas, as well as by transfer to existing gases within reaction zone 207.

Gas hydrate formation is expected to occur in reaction zone 207, however some gas hydrate formation may also occur within mixing zone 205, depending on the thermodynamic conditions of the resulting water-gas mixture present. If the temperature and pressure condition of water-gas mixture 206 in mixing zone 205 is somewhat below the equilibrium hydrate formation temperature so that some degree of gas hydrate formation in mixing zone 205 could reasonably be expected, the water and gas injection rates into mixing zone 205 can be maintained such that the flow rate of water-gas mixture 206 through mixing zone 205 limits the time available for further growth of those gas hydrates, and spray through orifice 209 can be effectively maintained. Similarly, if some degree of gas hydrate formation in mixing zone 205 could reasonably be expected, removing at least a portion the exothermic heat generated before water-gas mixture 206 enters reaction zone 207 aids the overall process. For example, mixing zone 205 may be surrounded by an atmosphere of reduced temperature, so that exothermic heat produced in mixing zone 205 may conduct through the mixing zone 205 containment. In one embodiment, the mixing zone 205 is wholly included within a nozzle, and the nozzle is surrounded by the reduced temperature atmosphere of reaction zone 207.

Preferably the water temperature, the water pressure, the gas temperature, the gas pressure, and the water and gas injection rates are maintained such that water-gas mixture 206 in mixing zone 205 has a temperature and pressure condition closely approximating a condition on the hydrate stability curve of the gas hydrate formed, so that the necessary cooling within reaction zone 207 may be mitigated. The conditions of water-gas mixture 206 within mixing zone 205 may be evaluated through thermodynamic analysis of the water temperature, the water pressure, the water injection rate, the gas temperature, the gas pressure, the gas injection rate, and the flow and thermal characteristics of mixing zone 205, as well as other factors with might impact the thermodynamic condition within mixing zone 205. Direct indication may also be utilized when temperature and pressure sensing instrumentation is present within mixing zone 205. However, the temperature and pressure condition of water-gas mixture 206 is not limiting within the method. Within the method, it is only necessary that a differential pressure between water-gas mixture 206 and reaction zone 207 be sufficient to create a spray of water-gas droplets into reaction zone 207, and be sufficient such that the hydrate-forming gas comprising the plurality of water-gas droplets expands in reaction zone 207, and the expansion of the hydrate-forming gas cools and maintains at least some portion of the plurality of water-gas droplets at a hydrate forming temperature.

Figure 3:
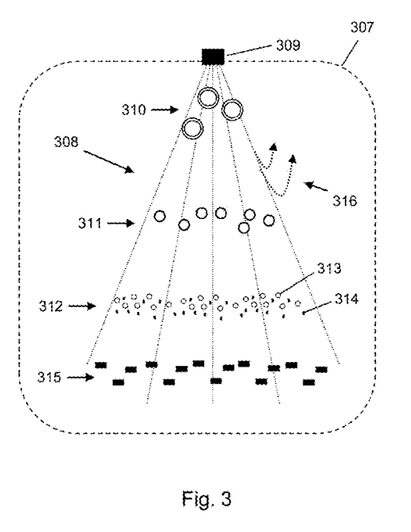
FIG. 3 illustrates the expansion of a hydrate-forming gas in the reaction zone.

A primary advantage to the novel method is a dramatically reduced induction time. In the process as disclosed herein, induction times on the order of 1 second have been achieved for the formation of methane hydrates. This decrease in the required induction time without additional mixing or cooling infrastructure is a significant advantage to the disclosed process The mechanism leading to the dramatically reduced induction time results from injecting hydrate-forming gas and water into a reaction zone as a water-gas mixture comprised of a plurality of water-gas droplets and allowing the hydrate-forming gas in the water-gas droplets to expand to the lower reaction zone pressure. The effect of the expansion in the water-gas mixture is further illustrated with reference to FIG. 3. FIG. 3 shows a spray generally indicated at 308 exiting from spray orifice 309 into reaction zone 307. Spray 308 is comprised of a plurality of water-gas droplets similar to spray 208, and reaction zone 307 has a reaction zone temperature and a reaction zone pressure, where the reaction zone temperature is less than the equilibrium hydrate formation temperature for the gas hydrate at the reaction zone pressure. At FIG. 3, a plurality of water-gas droplets generally indicated at 310 enters reaction zone 307 at time $t_0$. The water-gas droplets 310 are comprised of bubbles of the hydrate-forming gas surrounded by a film of liquid water, and at least the hydrate-forming gas within the film of liquid water is at the water-gas pressure of the mixing zone. This situation would be expected immediately upon exit from a mixing zone, such as mixing zone 205. Additionally, as discussed infra, gas hydrates formed in the mixing zone may enter reaction zone 307 along with water-gas droplets 310.

Upon entry into reaction zone 307, the hydrate-forming gas within the film of liquid water comprising water-gas droplets 310 commences expansion to the lower reaction zone pressure within reaction zone 307. The expansion of the hydrate-forming gas comprising water-gas droplets 310 breaks the liquid film surrounding the hydrate-forming gas and leads to reduced size droplets surrounded by liquid water, as generally indicated at 311 at time $t_1$, where $t_1 > t_0$. As a result of the gas-hydrate expansion as well as contact with the environment of reaction zone 308, the reduced size droplets 311 are reduced in temperature, and the hydrate-forming gas and the liquid water are in greater proximity. Additionally, some of the hydrate-forming gas and some of the water which comprised water-gas droplets 310 may fail to form the reduced size droplets 311 and may exit spray 308 and enter the atmosphere of reaction zone 307, as generally indicated at 316. Further, when gas hydrates formed in the mixing zone enter reaction zone 307, growth of these gas hydrates may occur as gas expansion drives more effective water distribution in reaction zone 307.

Continued expansion of the hydrate-forming gas comprising reduced size droplets 311 breaks the liquid films surrounding the reduced size droplets 311, and leads to a further size-reduced population generally indicated at 312 at time $t_2$, where $t_2 > t_1$. The further size-reduced population 312 has undergone further cooling and further mixing as result of the continued expansion to the reaction zone pressure, and the further size-reduced population 312 is comprised of further reduced bubbles 313 and gas hydrates 314 formed in reaction zone 307. As before, some of the hydrate-forming gas and some of the water which comprised water-gas droplets 311 may fail to form the further size reduced population 312 and may exit spray 308 and enter the atmosphere of reaction zone 307. The gas hydrates 314 thus formed are stable within reaction zone 307 and further grow to form hydrate crystals generally indicated at 315 at time $t_3$, where $t_3 > t_2$. Additionally, when gas hydrates formed in the mixing zone enter reaction zone 307, hydrate crystals 315 may be further comprised of those gas hydrates. The hydrate crystals 315 are thereby largely produced over the brief time period between $t_0$ and $t_3$.

In one embodiment, the hydrate-forming gas is methane, and the gas hydrate is methane hydrate, and the water temperature is from about 2° C. to about 15° C. and the water pressure is from about 500 psig to about 1200 psig, and the gas temperature is from about 5° C. to about 15° C. and the gas pressure is from about 500 psig to about 1200 psig, and the reaction zone pressure is from about 50 psig to about 200 psig less than the water-gas pressure, and the reaction zone temperature is from about 0.5° C. to about 2.0° C. In this embodiment, preferably the diameter of the water-gas droplets 310 is less than about 100 microns; more preferably in this embodiment, the diameter of the water-gas droplets 310 is less than about 60 microns.

In another embodiment, hydrate-forming gas—such as that exiting spray 308 and generally indicated at 316—is withdrawn from reaction zone 307 and recirculated to the gaseous stream, so that the hydrate-forming gas is subjected to the gas hydrate formation process in reaction zone 307 multiple times.

Figure 4:
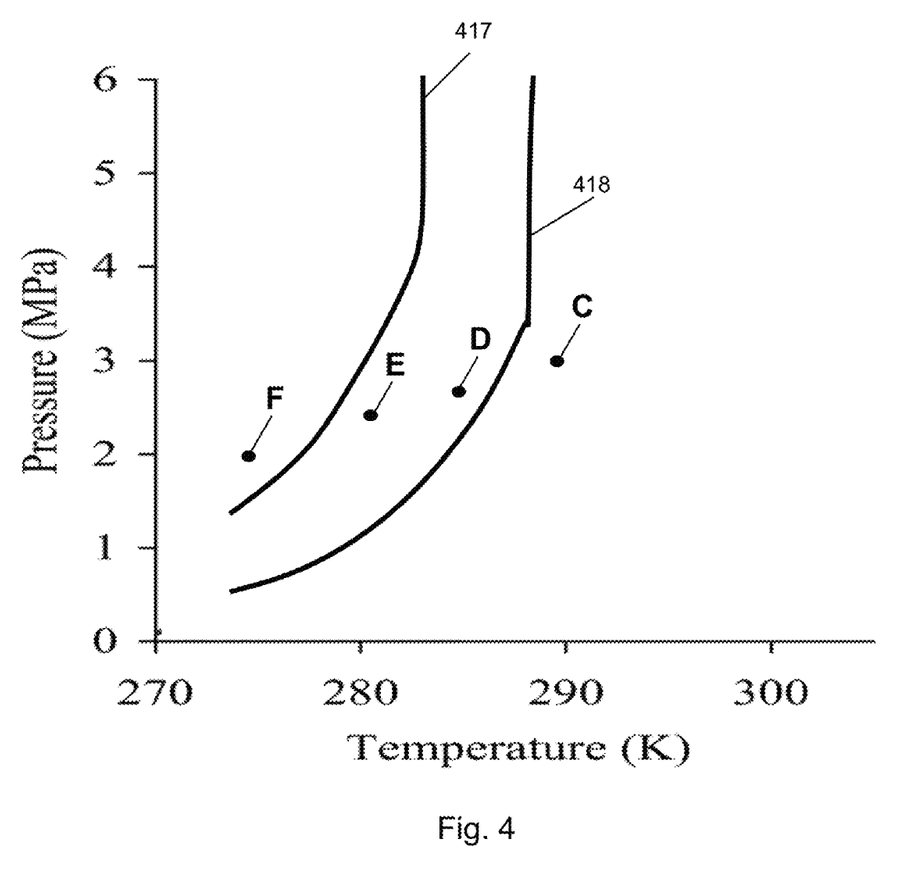
FIG. 4 illustrates a pressure-temperature diagram showing hydrate stability curves for a multi-constituent gas.

In another embodiment, the gaseous stream 204 entering the mixing zone 205 is comprised of at least a first hydrate-forming gas and at least a second hydrate-forming gas. For example, where the gaseous stream is comprised of two or more gases with the hydrate-stability curves of FIG. 4. At FIG. 4, the first hydrate-forming gas has hydrate-stability curve 418 and the second hydrate-forming gas has hydrate stability curve 417. In this embodiment, the method may first be conducted, for example, between points C and D to form a first gas hydrate using the disclosed method from the first hydrate-forming gas. Following formation of the first gas hydrate, the remaining gas comprised of the second hydrate forming gas may be withdrawn and the method may be conducted, for example, between points E and F for formation of the second gas hydrate. In this manner, the method may be utilized for the formation of gas hydrates from gaseous streams comprised of multiple hydrate-forming constituents. For example, the gaseous stream could be natural gas comprised of numerous light gases including $CH_4$, $CO_2$, $H_2S$, $N_2$, $C_2H_6$, He, Ar, Kr, Ne, and Xe, among others. By chaining together the method as disclosed herein, a pure methane hydrate may be formed and the remaining gases may be further separated as a hydrate and stored or otherwise disposed of.

In another embodiment, a processor is utilized to determine a model injection rate ratio into mixing zone 205, where the model injection rate ratio is a ratio of the water injection rate to the gas injection rate for the formation of gas hydrates in the reaction zone. The model injection rate ratio is based on the water-gas temperature and the water-gas pressure in mixing zone 205, which may be provided by direct indication or through analysis of parameters such as the water pressure and the water temperature of water flow 202 and the gas pressure and the gas temperature of gas flow 204. In operation, the water injection rate and the gas injection rate are adjusted to match the model injection rate ratio. The processor may be programmed to determine the model injection rate ratio using thermodynamic analysis and internal mixing atomization methodologies of the factors involved, as is known by those skilled in the art.

Description of the Apparatus

Figure 5:
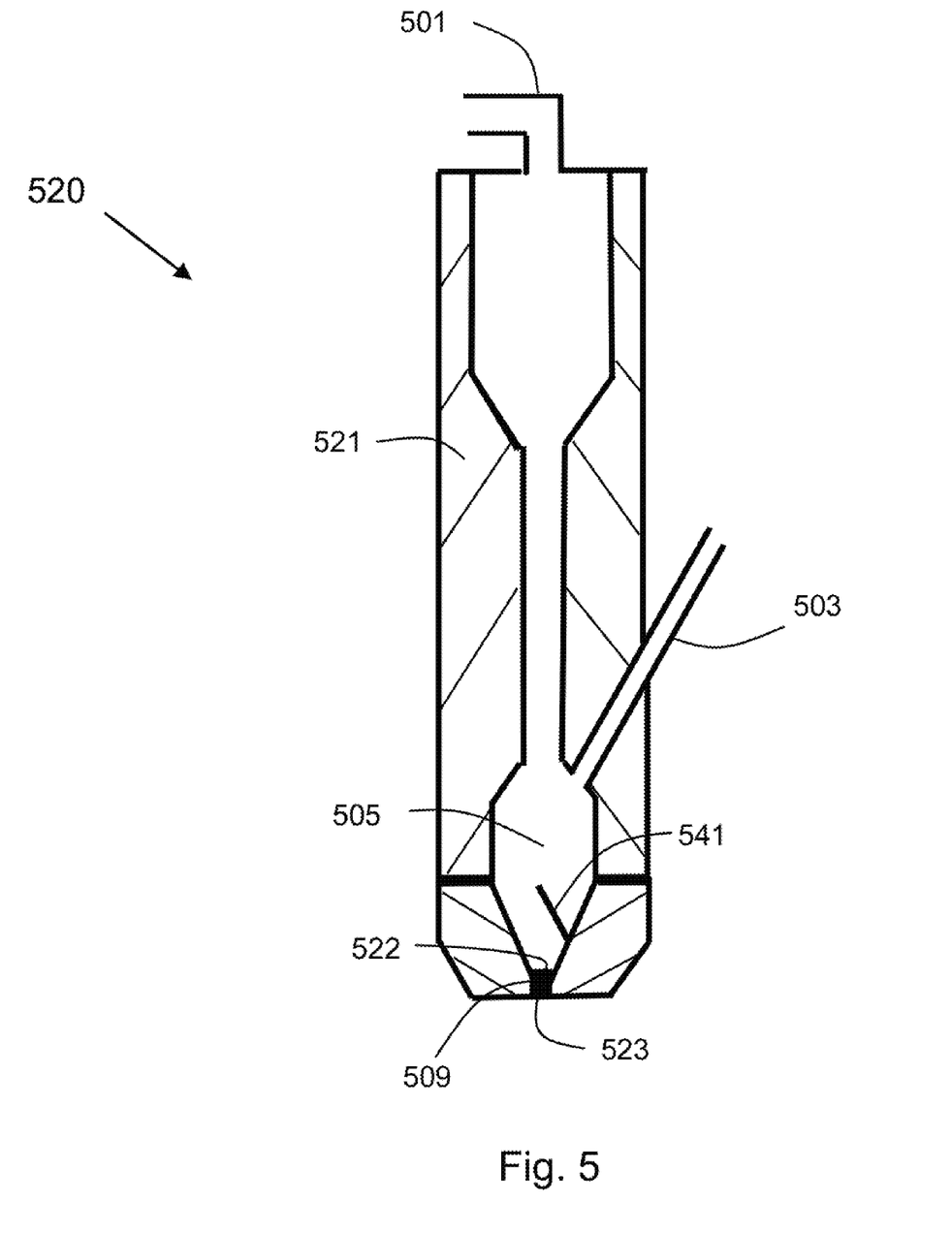
FIG. 5 illustrates a hydrate-formation nozzle suitable for use with the hydrate-forming method.
Figure 6:
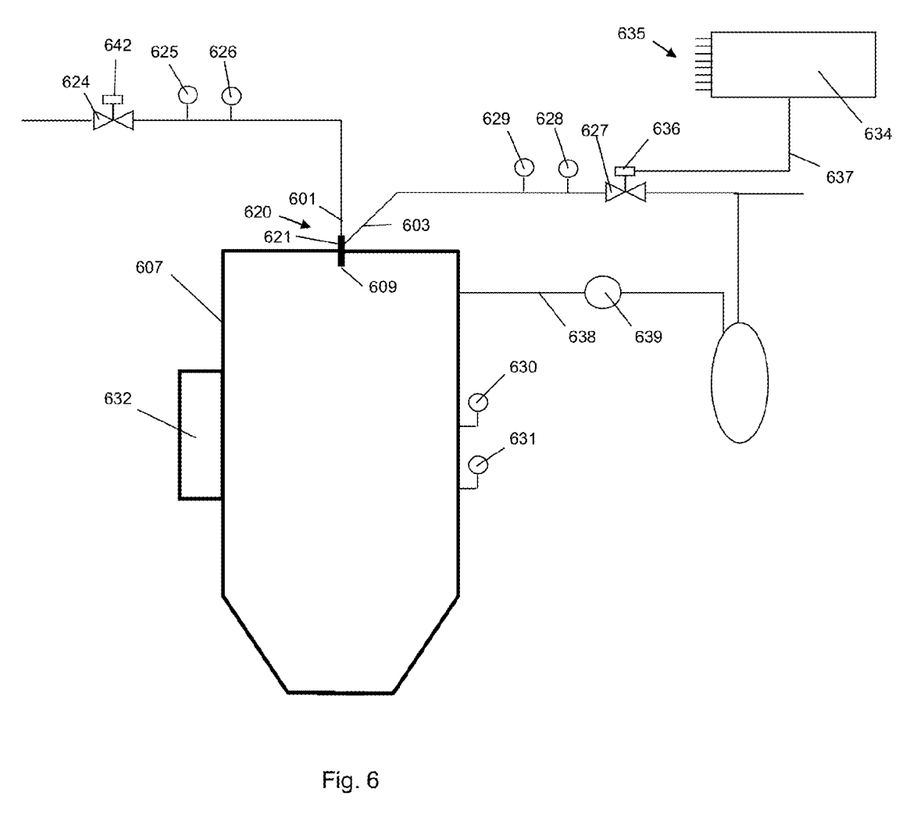
FIG. 6 illustrates an apparatus for the creation of gas hydrates using the hydrate-forming method.

An apparatus for forming gas hydrates using the method disclosed herein in illustrated at FIGS. 5 and 6.

FIG. 5 illustrates a nozzle 520 having water flow path 501 and gas flow path 503. Water flow path 501 and gas flow path 503 are in fluid communication with an enclosure 505. Further, a spray orifice 509 has an orifice inlet 522 and an orifice outlet 523. The spray orifice 509 is capable of receiving a flow at orifice inlet 522 and expelling the flow through the orifice outlet 523 as a plurality of fluid droplets when a sufficient positive differential pressure exists from orifice inlet 522 to orifice outlet 523. Spray orifice 509 is situated such that orifice inlet 522 is in fluid communication with enclosure

505. Further, swirl inserts or vanes 541 internal to nozzle body 521 and within enclosure 505 may be utilized to increase the mixing of gas and water while further reducing water-gas droplet size.

FIG. 5 illustrates an embodiment where the nozzle 520 has a nozzle body 521, and the enclosure 505 wholly contained within the nozzle body 521. The apparatus as disclosed here does not require that enclosure 505 be wholly enclosed within a nozzle body, however the arrangement of FIG. 5 depicts a significant advantage of the process, in that nozzle 520 can be designed with enclosure 505 as an inherent feature, greatly reducing any physical footprint of the apparatus that may be required.

The enclosure such as enclosure 505 further includes a means to determine a water-gas pressure. The means to determine the water-gas pressure is in fluid communication with the enclosure. The means to determine the water-gas pressure may be in fluid communication with the enclosure and may be a bellows, diaphragm, semiconductor strain sensor, or other sensors well known in the art, and may relay pressures of interest using an analog pneumatic, analog electronic, digital electronic signal, or using other methods well known in the art. Alternatively, the means to determine the water-gas pressure may be an evaluation of the water-gas pressure within the enclosure based on temperature, pressure, and mass flow conditions within a water flow path and a gas flow path such as water flow path 501 and gas flow path 503. Alternately, the means to determine the water-gas pressure may be an operator exercising visual observation of a spray from a spray orifice such as spray orifice 509.

FIG. 6 illustrates the remainder of the apparatus. At FIG. 6, the nozzle generally indicated at 620 is similar to the nozzle 520 of FIG. 5, such that nozzle 620 has a nozzle body 621, and an enclosure (not shown) is wholly contained within the nozzle body 621. Nozzle 620 further has water flow path 601 and gas flow path 603 in fluid communication with the enclosure (not shown). Water flow control means 624 is in fluid communication with water flow path 601, and gas flow control means 627 is in fluid communication with gas flow path 603. A spray orifice 609 is capable of receiving a flow from the enclosure (not shown) expelling the flow as a plurality of fluid droplets when a sufficient positive differential pressure across spray orifice 609. Spray orifice 609 may be an orifice plate, a venturi nozzle, an atomizer, or any means known in the art for receiving a two-phase, liquid-gas mixture and issuing the two-phase mixture as a plurality of droplets.

Water flow control means 624 may be any device or method known the art for flow control. Water flow control means 624 may be a throttle valve or other flow control mechanisms well known in the art, and may relay flow data of interest using an analog pneumatic, analog electronic, digital electronic signal, or using other methods well known in the art. Gas flow control means 627 may be any device or method known the art for flow control. Gas flow control means 627 may be a throttle valve or other flow control mechanisms well known in the art, and may relay flow data of interest using an analog pneumatic, analog electronic, digital electronic signal, or using other methods well known in the art.

The nozzle 620 and spray orifice 609 are arranged such that spray orifice 609 receives a flow from the enclosure (not shown) and issues a plurality of droplets into hydrate vessel 607. A hydrate vessel pressure indication 630 is in fluid communication with hydrate vessel 607. The hydrate vessel pressure indication 630 may be a bellows, diaphragm, semiconductor strain sensor, or other sensors well known in the art, and may relay pressures of interest using an analog pneumatic, analog electronic, digital electronic signal, or using other methods well known in the art. Further, a hydrate vessel temperature indication 631 is in thermal communication with hydrate vessel 607. The hydrate vessel temperature indication 631 may be a thermocouple, a thermistor, a resistance temperature detector, a pyrometer, or other sensors well known in the art, and may relay temperatures of interest using an analog, analog electronic, digital electronic signal, or using other methods well known in the art.

A refrigeration means 632 is in thermal contact with hydrate vessel 607. Refrigeration means 632 may be any process capable of providing temperatures in hydrate vessel 607 and removing heat from hydrate vessel 607, such as a vapor compression cycle, a vapor absorption cycle, a gas cycle, non-cyclic refrigeration, thermoelectric refrigeration, or other processes well known in the art.

In operation, the apparatus of FIGS. 5 and 6 forms gas hydrates using the method disclosed herein by introducing a water flow through water flow path 601 and introducing a gaseous stream comprised of a hydrate-forming gas through gas flow path 603 into an enclosure, such as enclosure 505. The gas injection rate is maintained relative to the water injection rate such that the water and the hydrate-forming gas mix in enclosure 505 form a water-gas mixture at a water-gas pressure. The resulting water-gas mixture is sprayed into hydrate vessel 607 as a plurality of water-gas droplets. Hydrate vessel 607 is maintained at a reaction zone pressure indicated by hydrate vessel pressure indication 630, and a reaction zone temperature indicated by hydrate vessel temperature indication 631. The reaction temperature and the reaction zone pressure are controlled by refrigeration means 632. These parameters may also be controlled to some degree by the water injection rate and the gas injection rate, and the thermodynamic conditions of the water flow and the gaseous stream. Hydrate vessel 607 is maintained in a condition such that the reaction zone temperature is less than the equilibrium hydrate formation temperature for the gas hydrate at the reaction zone pressure. Further, the reaction zone pressure is sufficiently less than the water-gas pressure such the expansion of the hydrate-forming gas cools at least some portion of the plurality of water-gas droplets from the water-gas temperature to a hydrate forming temperature. The sufficiency of the reaction zone temperature and reaction zone pressure may be determined through visual observation of hydrate crystal formation or other diagnostic evaluation of the products formed, for example, Raman Spectrum analysis.

In an embodiment, the apparatus is further comprised of a water pressure indication 625 in fluid communication with the water flow path 601, and a water temperature indication 626 in thermal communication with the water flow path 601. The water pressure indication 625 may be a bellows, diaphragm, semiconductor strain sensor, or other sensors well known in the art, and may relay pressures of interest using an analog pneumatic, analog electronic, digital electronic signal, or using other methods well known in the art. The water temperature indication 626 may be a thermocouple, a thermistor, a resistance temperature detector, a pyrometer, or other sensors well known in the art, and may relay temperatures of interest using an analog, analog electronic, digital electronic signal, or using other methods well known in the art.

In an embodiment, the apparatus is further comprised of a gas pressure indication 628 in fluid communication with the gas flow path 603, and a gas temperature indication 629 in thermal communication with the gas flow path 603. The gas pressure indication 628 may be a bellows, diaphragm, semiconductor strain sensor, or other sensors well known in the art, and may relay pressures of interest using an analog pneumatic, analog electronic, digital electronic signal, or using other methods well known in the art. The gas temperature indication 629 may be a thermocouple, a thermistor, a resistance temperature detector, a pyrometer, or other sensors well known in the art, and may relay temperatures of interest using an analog, analog electronic, digital electronic signal, or using other methods well known in the art.

In an embodiment, the enclosure may be arranged such that exothermic heat which may be produced in the enclosure may conduct through the enclosure containment. In one embodiment using a nozzle similar to nozzle 520, having enclosure 505 wholly contained within the nozzle body 521, nozzle 520 is at least partially surrounded by the volume within hydrate vessel 607, so that during operation the reduced temperature atmosphere of hydrate vessel 607 may act drive the conduction of exothermic heat generated within enclosure 505 through a portion of nozzle body 521.

In an embodiment, the apparatus of FIGS. 5 and 6 may be further comprised of a recirculation line 638 for the withdrawal of hydrate-forming gas—such as that exiting spray 308 and generally indicated at 316—from hydrate vessel 607. The hydrate-forming gas may be recirculated to gas flow path 603 to join the gaseous stream, so that the hydrate-forming gas is subjected to the gas hydrate formation process in hydrate vessel 607 multiple times. A recirculating means such as recirculation pump 639 may provide any motive force necessary for the recirculation.

In an embodiment, the apparatus of FIGS. 5 and 6 is further comprised of a means for determining an enclosure temperature in thermal communication with an enclosure such as enclosure 505. The means for determining the enclosure temperature may be a thermocouple, a thermistor, a resistance temperature detector, a pyrometer, or other sensors well known in the art, and may relay temperatures of interest using an analog, analog electronic, digital electronic signal, or using other methods well known in the art.

Figure 7:
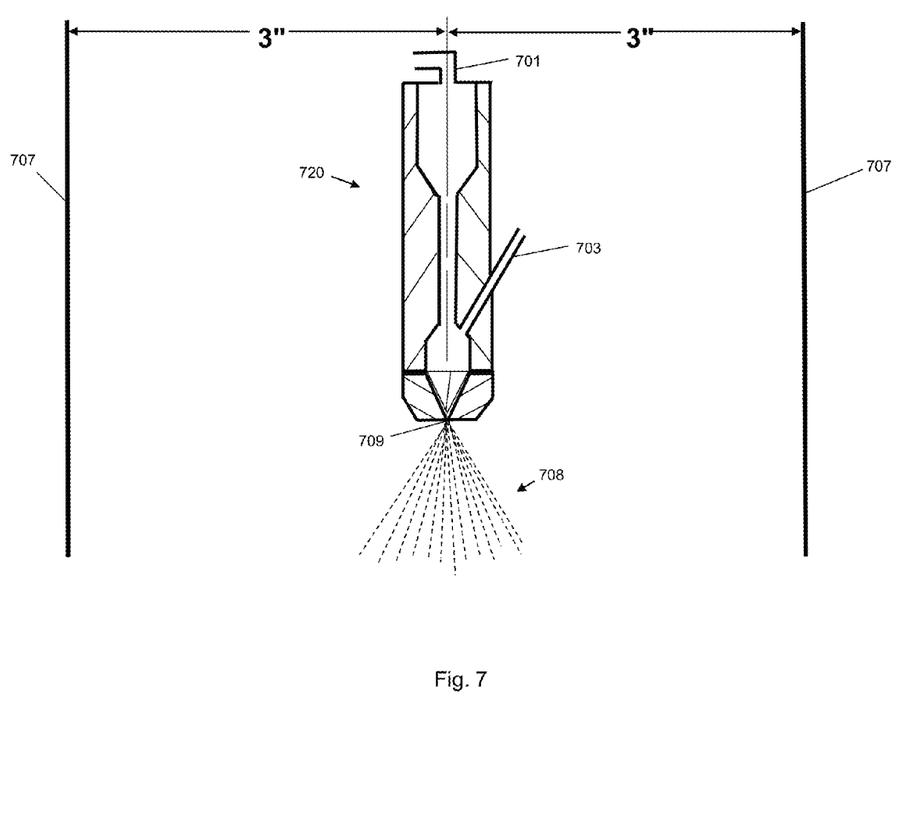
FIG. 7 illustrates a particular embodiment of the hydrate-forming method.

In an embodiment, the apparatus of FIG. 6 may be further comprised of processor 634 in data communication with at least the means for determining the enclosure pressure, the means for determining the enclosure temperature, hydrate vessel pressure indication 630, and hydrate vessel temperature indication 631 through data communication ports generally indicated at 635. Processor 634 may be programmed to determine a model flow rate ratio, where the model flow rate ratio is a ratio of the water injection rate through water flow path 601 to the gas injection rate through gas flow path 603 in order to form of gas hydrates in hydrate vessel 607. Further, gas flow control means 627 may have an automatic adjustment means 636, where the automatic adjustment means 636 is capable of receiving a position signal indicative of the model flow rate ratio from processor 634 through data path 637, and adjusting gas flow control means 627 based on the position signal. Similarly, water flow control means 624 may have an automatic adjustment means 642, where the automatic adjustment means 642 is capable of receiving a position signal indicative of the model gas flow rate from processor 634, and adjusting water flow control means 624 based on the position signal. The automatic adjustment means 636 and 642 may be a hydraulic or electric servomotor, a variable solenoid, or other automatic adjustment means well known in the art Model Results FIG. 7 illustrates an apparatus used to conduct the method as disclosed herein for the formation of methane hydrates. A water flow was introduced through water flow path 701 through a nozzle generally indicated at 720. The water flow was maintained at a water temperature between about 2° C. to about 15° C. and a water pressure from about 500 psig to about 1200 psig, and supplied to water flow path 701 at a water injection rate of from about 50 ml/min to about 200 ml/min. A gaseous stream comprised of methane as the hydrate-forming gas was introduced through gas flow path 703. The gaseous stream was introduced at a gas temperature from about 5° C. to about 15° C. and the gas pressure from about 500 psig to about 1200 psig.

Figure 8:
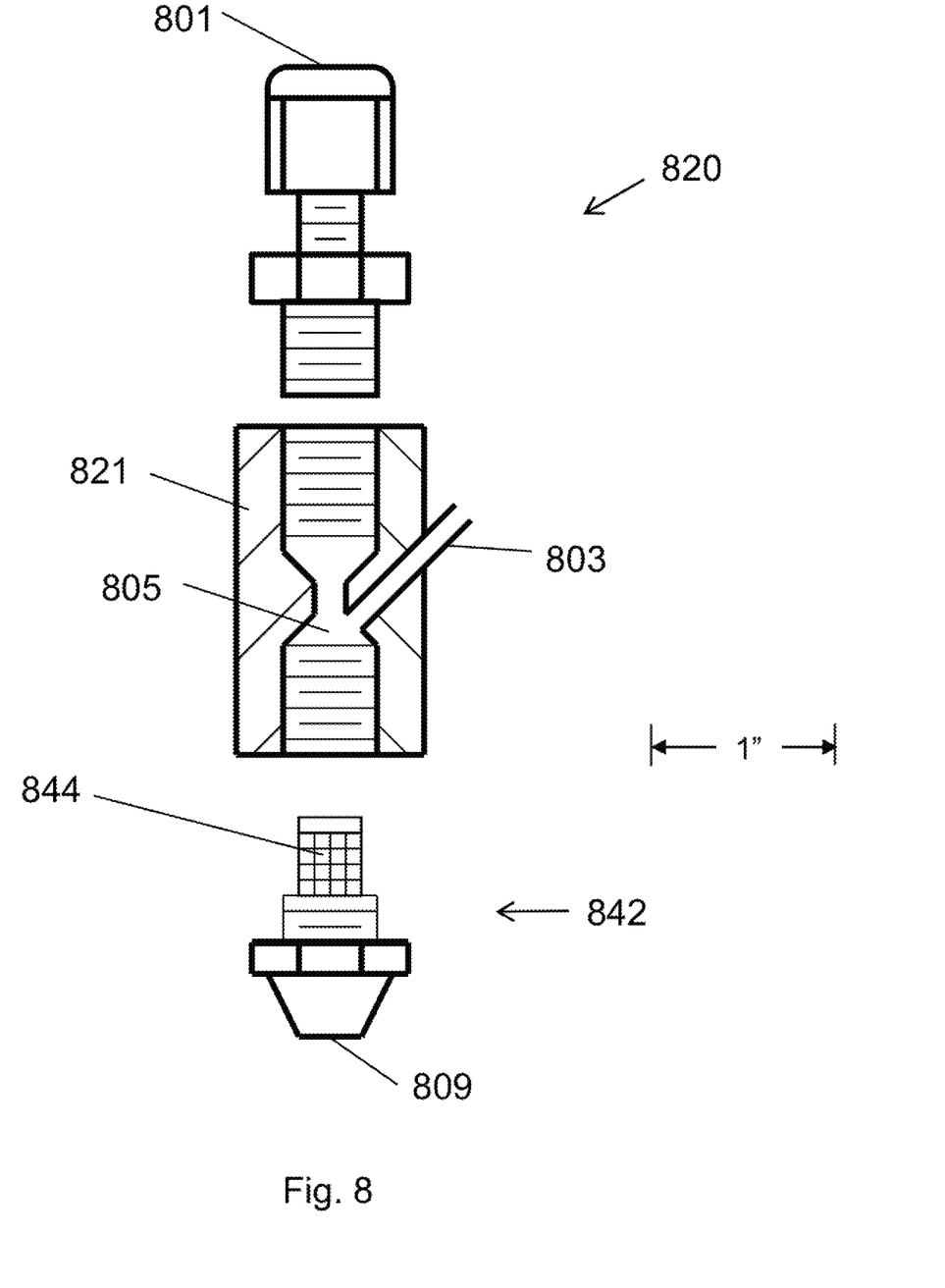
FIG. 8 illustrates a particular embodiment of a nozzle.

FIG. 8 illustrates an exploded view of an exemplary nozzle generally indicated at 820 and similar to nozzle 720, showing water flow path 801, gas flow path 803, nozzle body 821, and nozzle fitting 842 comprised of strainer or sintered filter 844, a swirl insert (not shown), and spray orifice 809. Enclosure 805 results when the illustrated sections are fastened using the threads as shown. Water flow path 801 is comprised of a ⅛ inch line and a tube fitting, such as a SWAGELOK SS-200-1-4 fitting. Gas flow path 803 is ⅛ inch diameter. Nozzle body 821 was designed and constructed to receive a fluid through water flow path 801, and machined to produce gas flow path 803, creating enclosure 805. This design allowed for the conversion and connection of a single fluid nozzle to be utilized as a twin fluid nozzle. The strainer or sintered filter 844 provides further mixing in enclosure 805 and may produce gas bubbles less than 100 microns in diameter. The water-gas mixture may be further atomized when passing though the swirl insert. Atomization may be further provided when the water-gas mixture passes through spray orifice 809. Spray orifice 809 may be a commercially available shear insert and nozzle orifice 0.00875 to 0.0150 inches in diameter. The single-fluid nozzle was commercially available from DELEVAN SPRAY TECHNOLOGIES, Bamberg, S.C., or SPRAYING SYSTEMS CO., Wheaton, Ill.

Nozzle 720 had a nozzle fitting similar to nozzle fitting 842, and spray orifice 709 produced a spray 708 into a hydrate vessel 707. Hydrate vessel 707 was a 15L cell having physical dimension approximately to scale with the spatial dimension included at FIG. 7. Hydrate vessel 707 was maintained at a hydrate vessel temperature from about 0.5° C. to about 2.0° C. and a hydrate vessel pressure sufficient to maintain 50-200 psid across spray orifice 709. Nozzle 720 was substantially surrounded by the atmosphere of hydrate vessel 707. Under these conditions spray orifice 709 produced a water-gas spray comprised of droplets having a less than 60 micron diameter. Methane hydrate formation in vessel 707 was observed with an induction time of approximately 1 second.

It is understood that the values expressed above are not limiting within the method and apparatus, but are merely expressed as exemplary conditions utilized during the experiments that were conducted.

Figure 9:
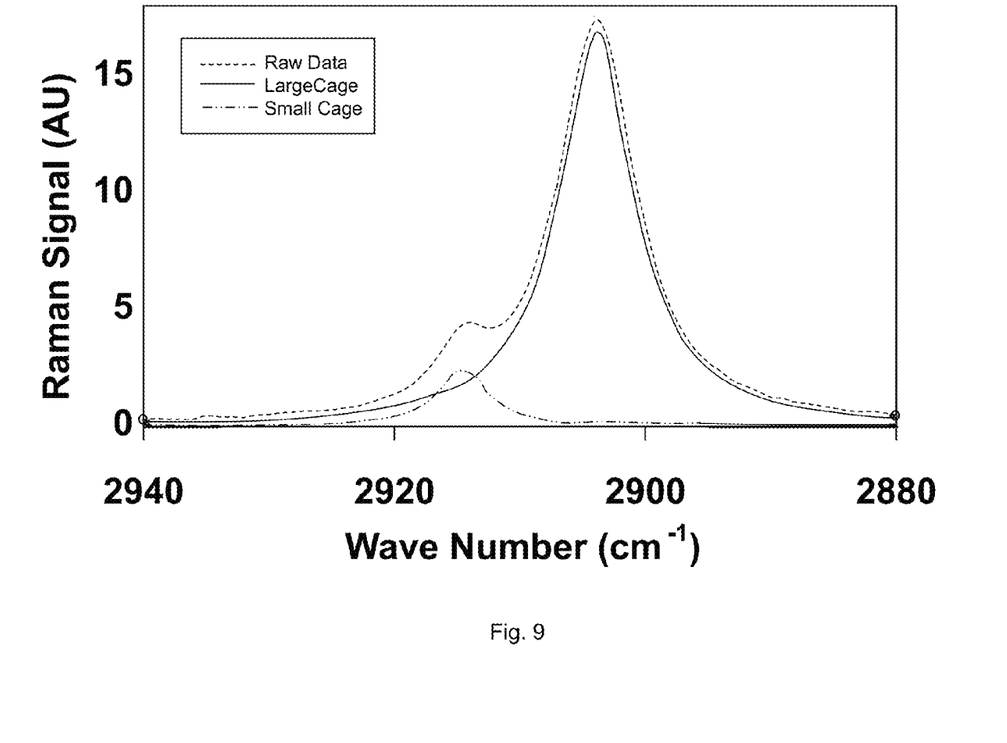
FIG. 9 illustrates a Raman spectrum of methane hydrates produced in a particular embodiment.

Methane hydrate formation was confirmed by visual observation of methane hydrate crystals in vessel 707 as well as the subsequent Raman Spectrum analysis on hydrate samples shown at FIG. 9, indicating the formation of methane hydrate using the method and apparatus as outlined within this disclosure.

Thus, the disclosure provides a method and apparatus for the formation of gas hydrates using a two-phase mixture of water and the hydrate-forming gas, where the exothermic heat of gas hydrate formation is effectively removed without reliance on contact between reactor walls and other heat transfer surfaces, and without reliance on water sub-cooling systems generating significant parasitic loads. The water and the gas-forming hydrate are introduced into a hydrate-forming reactor as a mixture, so that reliance on shear forces or water-gas intermingling for mixing within the reactor itself can be mitigated. Further, exothermic heat removal is accommodated by the thermodynamic response of the mixture to the hydrate reactor conditions, and the thermodynamic response simultaneously aids in further contact between the water and the hydrate-forming gas of the mixture.

Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of elements or sequences, or the use of numbers, letters, or other designations therefore, is not intended to limit the claimed processes to any order except as may be specified in the claims. Accordingly, the invention is limited only by the following claims and equivalents thereto.

All publications and patent documents cited in this application are incorporated by reference in their entirety for purposes to the same extent as if each individual publication or patent document were so individually denoted.

What is claimed is:

1. A method of forming a gas hydrate, where the gas hydrate is comprised of water and a hydrate-forming gas, comprising:
    injecting the water into a mixing zone at a water injection rate;
    admitting a gaseous stream comprised of the hydrate-forming gas into the mixing zone at a gas injection rate, and maintaining the gas injection rate relative to the water injection rate such that the water and the hydrate-forming gas mix in the mixing zone and form a water-gas mixture in the mixing zone, where the water-gas mixture is comprised of bubbles of the hydrate-forming gas separated by an interstitial water, where the interstitial water is comprised of the water, and where the water-gas mixture has a water-gas pressure; and
    spraying the water-gas mixture through an orifice into a reaction zone such that the water-gas mixture enters the reaction zone as a plurality of water-gas droplets, where the water-gas droplets are comprised of the hydrate-forming gas surrounded by a film of the water, and where the reaction zone has a reaction zone pressure and a reaction zone temperature, where the reaction zone temperature is less than or equal to the equilibrium hydrate formation temperature for the gas hydrate at the reaction zone pressure, and where the reaction zone pressure is sufficiently less than the water-gas pressure such the hydrate-forming gas comprising the plurality of water-gas droplets expands, and the expansion of the hydrate-forming gas cools and maintains at least some portion of the plurality of water-gas droplets at a hydrate forming temperature, where the hydrate forming temperature is less than or equal to the equilibrium hydrate formation temperature for the gas hydrate at the reaction zone pressure, such that some portion of the water and some portion of the hydrate-forming gas comprising the plurality of water-gas droplets form the gas hydrate in the reaction zone,
    thereby forming the gas hydrate, where the gas hydrate is comprised of water and the hydrate-forming gas.

2. The method of claim 1 where the water-gas mixture in the mixing zone is comprised of the water, the hydrate forming gas, and the gas hydrate, and where the gas injection rate is further maintained relative to the water injection rate such that at least a portion of the gas hydrates comprising the water-gas mixture in the mixing zone are transported through the orifice into the reaction zone.

3. The method of claim 2 including cooling the mixing zone and removing an exothermic heat from the mixing zone, where the exothermic heat is generated by the formation of the gas hydrates comprising the water-gas mixture in the mixing zone.

4. The method of claim 2 where the water-gas mixture has a water-gas temperature, where the water-gas temperature is equal to or below the equilibrium hydrate formation temperature for the water-gas pressure.

5. The method of claim 1 where the water-gas mixture has a water-gas temperature, where the water-gas temperature is above the equilibrium hydrate formation temperature for the water-gas pressure.

6. The method of claim 1 where the reaction zone pressure is from about 50 psig to about 200 psig less than the water-gas pressure, and where some portion of the plurality of water-gas droplets enters the reaction zone with a diameter less than 100 microns.

7. The method of claim 1 where the gaseous stream is natural gas, and the hydrate-forming gas is methane, and the gas hydrate is methane hydrate, and where the water temperature is from about 2° C. to about 15° C. and the water pressure is from about 500 psig to about 1200 psig, and where the gas temperature is from about 5° C. to about 15° C. and the gas pressure is from about 500 psig to about 1200 psig, and where the reaction zone pressure is from about 50 psig to about 200 psig less than the water-gas pressure, and where the reaction zone temperature is from about 0.5° C. to about 2.0° C.

8. The method of claim 1 further comprising:
    withdrawing some portion of a remaining gas from the reaction zone, where the remaining gas is comprised of the gaseous stream less the some portion of the hydrate-forming gas forming the gas hydrate, and recirculating the some portion of the remaining gas to the gas flow path.

9. The method of claim 1 further comprising:
    withdrawing some portion of a remaining gas from the reaction zone, where the remaining gas is comprised of the gaseous stream less the some portion of the hydrate-forming gas forming the gas hydrate, and where the some portion of the remaining gas is comprised of a second hydrate-forming gas; and
    forming a second gas hydrate, where the second gas hydrate is comprised of a second water and the second hydrate-forming gas, by using a second mixing zone and a second reaction zone, and by repeating the steps of claim 1 using the second mixing zone as the mixing zone, the second water as the water, the some portion of the remaining gas as the gaseous stream comprised of the hydrate-forming gas, the second hydrate forming gas as the hydrate forming gas, and the second reaction zone as the reaction zone.

10. The method of claim 1 where the water-gas mixture has a water-gas temperature and further comprising:
    programming a processor to determine a model injection rate ratio into the mixing zone based on at least the water-gas temperature and the water-gas pressure, where the model injection rate ratio is a ratio of the water injection rate to the gas injection rate for the formation of gas hydrates in the reaction zone;
    providing the water-gas temperature and the water-gas pressure to the processor, and determining the model injection rate ratio using the processor; and
    adjusting the gas injection rate and the water injection rate so that the ratio of the water injection rate to the gas injection rate substantially matches the model gas injection rate.

11. The method of claim 10 where the water has a water temperature and a water pressure, and where the gaseous stream has a gas temperature and a gas pressure, and further comprising:
  determining the water-gas temperature and the water-gas pressure based on at least the water injection rate, the water pressure, the water temperature, the gas injection rate, the gas pressure, and the gas temperature.

12. The method of claim 1 further comprised of adjusting the water-gas pressure of the water-gas mixture by altering the water injection rate and the gas injection rate.

13. The method of claim 1 further comprised of adjusting the water-gas temperature of the water-gas mixture by altering the water injection rate and the gas injection rate.

14. The method of claim 1 where the injecting step is accomplished by flowing the water in a water flow path in fluid communication with the mixing zone, and where the admitting step is accomplished by flowing the gaseous stream comprised of the hydrate-forming gas in a gas flow path in fluid communication with the mixing zone, thereby forming the water-gas mixture in the mixing zone, where the mixing zone is enclosed within a nozzle comprised of a nozzle body and further comprised of the orifice, where the orifice has an orifice inlet and an orifice outlet, where the orifice inlet is in fluid communication with the mixing zone and the orifice outlet is in fluid communication with the reaction zone, and where the spraying step is accomplished by forcing the water-gas mixture into the orifice inlet and discharging the water-gas mixture from the orifice outlet, thereby spraying the water-gas mixture through the orifice into the reaction zone.

15. The method of claim 14 where the reaction zone is enclosed by the interior of a hydrate vessel where the interior of the hydrate vessel is at the reaction zone temperature and the reaction zone pressure, and where the interior of the hydrate vessel is in fluid communication with the orifice outlet such that the water-gas mixture is discharged from the orifice outlet into the interior of the hydrate vessel, thereby forming the gas hydrate in the interior of the hydrate vessel.

16. The method of claim 15 where the water temperature is from about 2° C. to about 15° C. and the water pressure is from about 500 psig to about 1200 psig, and where the gas temperature is from about 5° C. to about 15° C. and the gas pressure is from about 500 psig to about 1200 psig, and where the reaction zone pressure is from about 50 psig to about 200 psig less than the water-gas pressure, and where the reaction zone temperature is from about 0.5° C. to about 2.0° C.

17. The method of claim 16 where some portion of the plurality of water-gas droplets enters the reaction zone with a diameter less than 100 microns.

18. The method of claim 17 where the gaseous stream is natural gas, and the hydrate-forming gas is methane, and the gas hydrate is methane hydrate.

* * * * *